United States Patent [19]

Hunt et al.

[11] Patent Number: 4,505,161

[45] Date of Patent: Mar. 19, 1985

[54] MINERAL SAMPLE PRESERVATION PROCESS

[75] Inventors: Patricia K. Hunt, Solon; Steven J. Waisala, Aurora, both of Ohio

[73] Assignee: The Standard Oil Company, Cleveland, Ohio

[21] Appl. No.: 478,381

[22] Filed: Mar. 24, 1983

[51] Int. Cl.³ ............................................. G01N 1/28
[52] U.S. Cl. ........................................ 73/863; 73/153
[58] Field of Search ................ 73/432 R, 432 Z, 38, 73/153, 863; 175/59, 226

[56] References Cited

U.S. PATENT DOCUMENTS

| | | |
|---|---|---|
| 2,662,401 | 12/1953 | Bailly . |
| 2,893,691 | 7/1959 | Johnson ............................. 175/226 |
| 2,927,775 | 3/1960 | Hildebrandt ....................... 175/226 |
| 3,092,191 | 6/1963 | Mori et al. ......................... 175/226 |
| 3,123,158 | 3/1964 | Gallus ................................ 175/226 |
| 3,426,102 | 2/1969 | Solak . |
| 3,451,538 | 6/1969 | Trementozzi . |
| 3,540,577 | 11/1970 | Trementozzi . |
| 3,916,048 | 10/1975 | Walles . |
| 4,238,535 | 12/1980 | Talsma . |
| 4,265,948 | 5/1981 | Hays et al. . |

*Primary Examiner*—S. Clement Swisher
*Attorney, Agent, or Firm*—Debra L. Pawl; David J. Untener; Larry W. Evans

[57] ABSTRACT

Mineral samples are sealed in a nitrile barrier resin which prevents alterations in a sample between the time the sample is taken and the time the sample is analyzed. This resin provides chemical resistance to a core sample and good water vapor barrier properties and excellent oxygen barrier properties. The resin may be laminated with other materials to improve various properties.

19 Claims, No Drawings

MINERAL SAMPLE PRESERVATION PROCESS

BACKGROUND OF THE INVENTION

This invention relates to a new process for protecting mineral samples. A typical field for the application of this invention is in the sampling and testing of core samples from oil and gas and other types of wells. Although not limited to this use, the invention is described with respect to this use. In drilling oil, gas and other types of wells, it is conventional practice to take samples of the strata through which the drill bit is passing. By analyzing these samples with respect to such parameters as permeability, porosity, and fluid saturation, a great deal can be learned regarding the nature of the particular strata or horizon from which the core was taken. These tests are generally included in the generic term "core analysis" which allow the characteristics of a particular reservoir to be evaluated. Moreover, when combined with the same procedures in adjacent and distant wells this analysis provides a valuable aid in mapping the subsurface geology of a region.

The constant aim in obtaining core samples for subsequent analysis is to employ methods and techniques in the field that will ensure to the greatest possible extent that the core sample will be possessed of its original properties as it reaches the laboratory for analysis. It is evident that any intervening loss in moisture or oil content as well as any physical alterations, particularly those due to chemical interaction between the sample and the preservative material or inordinant temperature changes will result in erroneous interpretation of the characteristics of the subsurface strata from which the core was taken. Current methods do not provide a preservation process utilizing materials which provide satisfactory oxygen and water vapor barriers. The present invention is directed in part to improving techniques for core sampling in order to increase the reliability of data obtained therefrom. The method disclosed in the present invention utilizes materials which provide improved barrier properties, particularly against oxygen and water vapor transmission.

Different methods of core sample protection are known. A common method of protecting samples is to wrap the core first in polyvinylidene chloride (saran wrap) and then in aluminum foil. The foil is closed by crimping the edges and then the covered core is dipped in melted plastic such as B-60, which hardens into a seal. B-60 is a type of "Hot Melt Peel Coat Type II" made by Evans Manufacturing, Inc., in Warren, Mich. This method of protecting core samples is inadequate because the saran wrap is not chemically inert to the sample and disintegrates, oxygen and water vapor pass through the crimped seal, and the foil is readily ripped or punctured. Therefore, when using this preservation method, the only material which can be considered as a preservative is the plastic coating. At best, the plastic coating acts as a poor oxyben and water vapor barrier and B-60 is not chemically resistant to the core sample.

Another method of core sample preservation is to cast the sample in a plastic jacket as disclosed by Bailly in U.S. Pat. No. 2,662,401. This method requires the addition of a catalyst and accelerator to a heated liquid plastic. Coordination of gel time, the time necessary to cast the sample and the temperature rise in the plastic while gelling makes this method complicated and undesirable to use in the field. Furthermore, if the gel time is too short, stresses and strains are created causing cracking of the plastic, thereby defeating the preservative purpose of the plastic. Moreover, although Bailly teaches a plastic material possessing the desired qualities of chemical inactivity to the sample, oil and water barrier properties, and non-adsorbency of the sample gases, Bailly does not teach that the plastic material act as an oxygen barrier against oxygen entering the sample from the exterior. Bailly also does not teach the use of a layered or laminated material.

SUMMARY

This invention relates to a process for preserving mineral samples comprising sealing said sample within a material comprising a nitrile oxygen barrier resin formed by the polymerization of 55 to 90 weight percent of an olefinically unsaturated monomernitrile with a remaining proportion of at least one monovinyl monomer copolymerizable with said nitrile optionally in the presence of a preformed diene rubber.

In an alternate embodiment, this invention relates to a process for preserving mineral samples comprising sealing said sample within at least two layers of material, said layers of material comprising a layer (a) next to said sample comprising a nitrile oxygen barrier resin formed by the polymerization of 55 to 90 weight percent of an olefinically unsaturated monomer nitrile with a remaining proportion of at least one monovinyl monomer copolymerizable with said nitrile optionally in the presence of a preformed diene rubber, and a layer (b) comprising a material having water vapor barrier properties.

In accordance with the process of the present invention, the core sample is enclosed in a nitrile barrier material which is both chemically resistant to the sample and also possesses barrier properties, preferably that of oxygen resistance. Nitrile barrier materials and the processes for making the same are known in the art, particularly as in U.S. Pat. No. 3,426,102 which is herein incorporated by reference. This particular nitrile barrier resin is commercially available and sold by the Standard Oil Company of Ohio under the Trademark "Barex." Alternatively, the sample can be wrapped and sealed by one or more additional layers wherein at least one of said layers is a water barrier. The other layers which may be present either between the nitrile barrier resin and the water barrier or wrapped around the water barrier include adhesives, metals and other water and oxygen barrier materials. The layers may be individually applied or preformed into a laminate. Laminates of the nitrile barrier resin are also known in the art, as disclosed in U.S. Pat. No. 4,339,502 which is herein incorporated by reference. Furthermore, methods of producing laminates are known in the art, and include coextrusion, thermoforming and metallizing, which is disclosed in Walles, U.S. Pat. No. 3,916,048.

This invention further relates to a package comprising a core sample completely enveloped by the above described materials. It is preferred that the material used to wrap the sample be capable of shaping itself to the contours of the sample under ambient conditions existing at the field site.

DETAILED DESCRIPTION

The material used to seal the core sample in the process of this invention provides an oxygen and water vapor barrier. It is desirable to prevent the sample from oxidizing or drying out, therefore minimal exposure to oxygen and minimal water loss is necessary to prevent alteration of the composition of the core sample. It is preferred that the oxygen transmission rate of this material be less than 1.0 cc-mil/100 sq. in. 24 hr. atm. and the water vapor transmission rate equal to or less than 5.0 g-mil/100 sq. in. 24 hr. Furthermore, this material provides chemical resistance to the core sample. It is of the utmost importance that the material remain chemically inert to the sample so as to maintain the integrity of the material and its preservative qualities and to prevent sample alterations.

This material comprises a major proportion of the monounsaturated nitrile, a minor proportion of a monovinyl monomer component copolymerizable with said nitrile, and optionally a performed diene rubber.

The monounsaturated nitrile useful in this invention includes the alpha, beta olefinically unsaturated mononitriles having the structure:

$$CH_2=C(R)-CN$$

wherein R is hydrogen, a lower alkyl group having from 1 to 4 carbon atoms, or a halogen. Such compounds include acrylonitrile, alpha-chloroacrylonitrile, alpha-fluoroacrylonitrile, methacrylonitrile, ethylacrylonitrile and the like. The most preferred unsaturated nitriles are acrylonitrile and methacrylonitrile and mixtures thereof. The preferred weight percent range of the nitrile in the barrier resin is from 55 to 90 weight percent with 60 to 85 weight percent being especially preferred.

As the acrylonitrile content of the polymer exceeds 90% and approaches 100 weight percent, it becomes extremely difficult to shape the polymer in conventional plastic forming equipment. Upon heating to more than 220° C., polymers containing more than 90% acrylonitrile retain sufficient crystallinity to preclude flow. When heated to the still higher temperatures that are required to melt the crystalline acrylonitrile chains the polymer rapidly degrads as shown by discoloration and reduced solubility in dimethyl formamide. However, the presence of at least one comonomer in the acrylonitrile polymers of this invention either prevents long sequences of acrylonitrile placement which give rise to crystallinity or minimizes crystal size and perfection. This provides the polymer with a lower melting temperature range and good flow behavior at lower temperatures. As a result, the polymers not only exhibit good barrier properties but also have the critical properties which allow them to be readily shaped into films and bulky objects which meet the critical packaging requirements for the applications contemplated herein.

The balance of the barrier resin is prepared from one or more monovinyl monomer components which are copolymerizable with acrylonitrile. Examples of these copolymerizable monomers include the esters of olefinically unsaturated carboxylic acids, vinyl aromatic monomers, vinyl esters, alpha-olefins and vinyl ethers.

The esters of olefinically unsaturated carboxylic acids include those having the structure:

$$CH_2=C(R_1)-COOR_2$$

where $R_1$ is hydrogen, an alkyl group having from 1 to 4 carbon atoms or a halogen, and $R_2$ is an alkyl group having from 1 to 6 carbon atoms. Compounds of this type include methylacrylate, ethylacrylate, the propyl acrylates, the butyl acrylates, the amyl acrylates, the hexyl acrylates, methylmethacrylate, ethylmethacrylate, the propyl methacrylates, the butyl methacrylates, the amyl methacrylates, and hexyl methacrylates, methyl alpha-chloro acrylate, ethyl alpha-chloro acrylate and the like. Most preferred in this invention are methylacrylate, ethylacrylate, methylmethacrylate and ethylmethacrylate.

The alpha olefins useful in this invention include those having at least 4 and as many as 10 carbon atoms and having the following structure:

$$CH_2=C(R_4)-R_3$$

wherein $R_3$ and $R_4$ are alkyl groups having from 1 to 7 carbon atoms and more specifically isobutylene, 2-methylbutene-1, 2-methylpentene-1, 2-methylhexene-1, 2-methylheptene-1, 2-methyloctene-1, 2-methylbutene-1, 2-propylpentene-1 and the like. Most preferred is isobutylene.

The vinyl ethers suitable for use in this invention have the following general formula:

$$CH_2=CH-O-R_5$$

wherein $R_5$ is an alkyl group having from 1 to 8 carbon atoms, an aryl group of from 6 to 10 carbons or a monovalent aliphatic radical of from 2 to 10 carbon atoms which may contain a hydrocarbon or oxygen, that is an aliphatic with ether linkages, and may also contain other substituents such as halogens, and carbonyls. The vinyl ethers include methyl vinyl ether, ethyl vinyl ether, the propyl vinyl ethers, the buty vinyl ethers, methyl isopropenyl ether, ethyl isopropenyl ether and the like. Most preferred are methyl vinyl ether, ethyl vinyl ether, the propyl vinyl ethers and the butyl vinyl ethers.

The vinyl esters useful in this invention include those having the following general formula:

$$CH_2=C(H)-O-\overset{O}{\underset{\|}{C}}-R_6$$

wherein $R_6$ is selected from the group comprising hydrogen, alkyl groups of from 1 to 10 carbon atoms, aryl groups of from 6 to 10 carbon atoms wherein said aryl group may also contain substituents such as halogens and alkyl groups attached to the nucleus. The vinyl esters include vinyl acetate, vinyl propienate, the vinyl butyrates, and the like. Most preferred in vinyl acetate.

The vinyl aromatic monomers useful in this invention include those having the following general formula:

$$CH_2=C(R_8)-R_7$$

wherein $R_7$ is hydrogen, chlorine or methyl and $R_8$ is an aromatic radical of 6 to 10 carbon atoms which may also contain substituents such as halogen and alkyl groups attached to the aromatic nucleus. Example of such compounds include styrene, alpha-methylstyrene, vinyltoluene, alpha-chlorostyrene, orthochlorostyrene, para-chlorostyrene, meta-chlorostyrene, orthomethylstyrene, para-methylstyrene, ethylstyrene, isopropyl-styrene, dichlorostyrene, vinyl naphthalene, and the like. An especially preferred aromatic monomer is styrene.

It is preferred that the optional preformed diene rubber be a copolymer of butadiene-1,3 and acrylonitrile.

The following Table I shows the water vapor transmission rate (WVTR) and oxygen transmission rate (OTR) of various core preservation materials. The substances were tested for their WVTR on a Mocon-IRd-2C and their OTR was determined on a Mocon Ox-Tran Ten Fifty. Temperature and relative humidity (R.H.) conditions were 100° F. and 100% R.H. for WVTR and 70° F. and 100% R.H. for OTR. Results are reported as the number of grams (g) (WVTR) or cubic centimeters (cc) (OTR) that will permeate through a 0.001 inch (1 mil) thick sheet of substance being tested that is 100 square inches (in.$^2$) in area over a 24 hour (hr.) period at atmospheric pressure (atm.). Those values with an asterick (*) represent values from the literature.

TABLE I

| | WVTR and OTR of Various Core Preservation Materials | |
|---|---|---|
| | Transmission Rate | |
| | Water Vapor | Oxygen |
| Preservative | g-mil | cc-mil |
| Material | 100 in$^2$ — 24 hr | 100 in$^2$ — 24 hr — atm |
| B-60 | 122 | 3015 |
| Saran wrap | 0.18 | 1.52 |
| Aluminum Foil | 0 | 0 |
| "Barex" | 5 | 0.8 |
| Polyethylene* | 1-2 | 500 |
| PVC* | 3.5-4 | 8-20 |

As can be seen from the above Table I, aluminum foil and saran wrap are good barriers. However, they are ineffective preservatives for essentially the reasons stated earlier. A crimped seal permits transmission of water vapor and oxygen and aluminum foil lacks the requisite strength. Saran is not chemically inert to core samples and its use is threfore undesirable. The Table also demonstrates that B-60 is not an effective barrier to water vapor and oxygen. "Barex" is a good water vapor barrier and an excellent oxygen barrier. To obtain enhanced water vapor barrier properties, it is desirable to combine polyethylene with "Barex" to form an alternative embodiment of the preservative material utilized in the present invention process. Although PVC also provides good barrier properties, polyethylene is preferred for its water vapor resistance. Furthermore, it can be seen how the barrier properties of the layered material can be greatly enhanced when aluminum foil comprises a layer in addition to Barex and the polyethylene layers.

ALTERNATE EMBODIMENT

In an alternative embodiment, the material used to seal the core sample in the process of this invention comprises at least two layers. The layer next to and in contact with the sample provides an oxygen barrier and comprises the chemically inert nitrile material hereinabove described.

Another layer of material required in the process of this invention comprises a water barrier substance which has a WVTR of less than 2.0 g-mil/100 sq. in. 24 hr. at 100° F. in 90% R.H. A WVTR less than 1.0 is preferred. Examples of materials which are useful as water barriers in the present invention include, but are not limited to, polyolefins such as polyethylene and polypropylene, polyethylene (PET), polyurethane copolymer (PUC) and aluminum foil. A low density polyethylene is preferred.

Substances comprising other layers may be included in the material to act as water vapor and oxygen barriers and/or protection against rough handling. The substances comprising these layers include aluminum foil, ethyl vinyl alcohol, wax, plastic and adhesives. The addition of foil to the nitrile resin and polyethylene layers makes the material opaque. Layers of nitrile resin and polyethylene only results in a transparent material which permits visual inspection of the sample.

The order in which the above described layers occur in the material can vary, except that the nitrile barrier resin layer must always be closest to and in contact with the core sample. When aluminum foil is included in the material, it is preferred that the aluminum foil layer is sandwiched between the nitrile oxygen barrier resin and the water barrier. It is also possible to have any number of layers of the above-described substances occurring in any order of combination, providing the nitrile barrier resin is the layer closest to the core sample.

The following Table II represents the data from an experiment wherein six core samples were tested for water loss during storage utilizing Applicant's invention method of preservation and the B-60 (seal-peal) method currently used in the art. Each core was presaturated to a known fluid saturation, preserved by the various indicated methods, stored for 3 months, and then tested for post-storage saturation.

Core samples 1 and 2 were preserved using the current seal-peal or B-60 method. The optimal version conists of a layer of high quality plastic wrap such as saran or Reynolds 904 film, followed by a layer of heavy duty aluminum foil, such as Kaiser Aluminum foil wrap, and two dips in B-60 peel coat. The minimal version consists of a layer of generic plastic wrap wrapped around the core followed by a layer of thinner generic foil wrap, and one dip in B-60 peel coat.

Core samples 'through 6 were preserved using Applicant's invention process of sealing the core sample with two different versions of a "Barex" laminate. In samples 3 through 6, the "Barex" laminate was sealed around the samples such that the Barex layer was in contact with the sample.

The opaque "Barex" laminate, consisting of a layer of aluminum foil sandwiched in between a layer of "Barex" and a layer of low density polyethylene, was used to preserve core number 3. Sample 4 was preserved in the transparent version of the material used in Applicants' invention process. The "transparent Barex" laminate was a material consisting of a layer of "Barex" and a layer of low density polyethylene.

Core samples 5 and 6 were preserved with the opaque and transparent "Barex" laminates respectively, coated with a microcrystalline wax dip.

The water saturation was determined by the Dean-Stark method. All data reported is accurate to within ±1.64%.

TABLE II

Comparison of Percent Water Loss During Storage of Core Samples Using Applicants' Invention Process and the B-60 Method

| Core # | Preservation Method | % Of Original Water Content Lost During Storage (±1.64%) |
| --- | --- | --- |
| 1 | Seal-Peel (B-60) Method Optimal Version | 20.41 |
| 2 | Seal-Peel (B-60) Method Minimal Version | 32.09 |
| 3 | Opaque "Barex" Laminate | −1.32 |
| 4 | Transparent "Barex" Laminate | 15.32 |
| 5 | Opaque "Barex" Laminate With Microcrystalline Wax Dip | 3.30 |
| 6 | Transparent "Barex" Laminate With Microcrystalline Wax Dip | 12.44% |

As can be seen from the data presented in the above Table II, any version of Applicant' preservation process, represented in core samples 3–6, provides a significantly better barrier against water loss than the currently used B-60 method for the preservation of samples 1 and 2.

The above described layers comprising the material used in the invention process can be applied to the core sample individually providing that the nitrile resin barrier layer is closest to the sample. Alternatively, the material can be applied as one laminated sheet wherein the nitrile resin is next to the sample.

The thickness of the material and the individual component layers may vary. Preferably, the thickness of the nitrile resin should be such that the material does not become brittle and lose its flexibility. The typical thickness for the transparent version of the material is 5 mil wherein a nitrile resin layer is 3 mil and the polyethylene is 2 mil and the opaque version of the material is typically 5.5 mil thick wherein the nitrile resin layer is 3 mil, the polyethylene is 2 mil and the aluminum foil is 0.5 mil thick.

Sealing the material, whether a single layer or multiple layers, can be achieved by any technique known in the art. One technique which works well is heat sealing the material around the sample. Another desired quality of the nitrile resin barrier is that it is heat sealable upon itself thereby eliminating the need for applied adhesives. However, adhesives may be required and used to seal the material used in this invention process and their use may depend upon the composition of the nitrile barrier resin and the water barrier.

For protection against shock and rough handling, the sealed sample can be coated over with an appropriate material such as B-60. However, it is recommended that microcrystalline wax be used because it provides additional water vapor and oxygen barrier protection in addition to protection against shock.

Although the above method of preserving core samples is effective, it is preferred that preservation occur in situ utilizing the materials described herein. In situ core preservation can readily be conducted by placing a pipe made of the material herein described, preferably of the transparent version, into the core barrel of the drilling device such that the core is automatically encased by said material as the core is drilled. When the core barrel is brought to the surface, the pipe of preservation matrial encasing the core sample can be pulled from the core barrel. The core sample can then be cut into convenient sized lengths, if desired, and then capped and sealed with the same material of this invention. Sealing of the caps can be achieved by any method known in the art, including heat sealing, the use of adhesives or screw-on caps if the pipe is threaded. It is preferred that the samples be sealed by threading the caps then applying an adhesive.

We claim:

1. A process for preserving mineral samples comprising:
    sealing said sample within a material comprising a nitrile oxygen barrier resin formed by the polymerization of 55 to 90 weight percent of an olefinically unsaturated monomernitrile with a remaining proportion of at least one monovinyl monomer copolymerizable with said nitrile optionally in the presence of a preformed diene rubber.

2. The process as in claim 1 wherein the material has an oxygen transmission rate of less than 1.0.

3. The process as in claim 1 wherein said olefinically unsaturated monomer nitrile comprises 60 to 85 percent of said nitrile oxygen barrier resin.

4. A process for preserving mineral samples comprising:
    sealing said sample within at least two layers of material, said layers of material comprising a layer (a) next to said sample comprising a nitrile oxygen barrier resin formed by the polymerization of 55 to 90 weight percent of an olefinically unsaturated monomer nitrile with a remaining proportion of at least one monovinyl monomer copolymerizable with said nitrile optionally in the presence of a preformed diene rubber, and a layer (b) comprising a material having water vapor barrier properties.

5. The process as in claim 4 wherein one or more additional layers (c) selected from the group consisting of metal, wax, plastic and adhesive seal the sample.

6. The process as in claim 4 or 5 wherein the layers are performed into a laminate prior to sealing said sample.

7. The process as in claim 4 wherein the layer (b) has a water vapor transmission rate equal to or less than 5.0.

8. The process as in claim 4 wherein the layer (a) has an oxygen transmission rate of less than 1.0.

9. The process as in claim 7 wherein the layer (b) has a water vapor transmission rate equal to or less than 2.0.

10. The process as in claim 4 wherein said olefinically unsaturated monomernitrile of the layer (a) comprises 60 to 85 percent of said nitrile oxygen barrier resin.

11. The process as in claim 5 wherein the layer (c) is aluminum foil.

12. The process as in claim 4 wherein the layer (b) is a low density polyethylene.

13. The process as in claim 4 wherein the unsaturated monomer nitrile of the layer (a) is acrylonitrile.

14. The process as in claim 4 wherein said layer (a) is acrylonitrile polymerized with ethylacrylate and said layer (b) is a material having a water vapor transmission rate equal to or less than 5.0.

15. The process as in claim 5 wherein said layer (a) is acrylonitrile polymerized with ethylacrylate; said layer (b) is aluminum foil; and said layer (c) is a low density polyethylene.

16. The process as in claim 5 wherein said layer (a) is acrylonitrile polymerized with ethylacrylate; said layer (b) is a low density polyethylene and said layer (c) is aluminum foil.

17. The process as in claim 15 wherein a layer of microcrystalline wax seals the sample after said sample is sealed within layers (a), (b) and (c).

18. A process for preserving mineral samples comprising:

sealing said sample within a laminate of at least two layers of material, said layers of material comprising a layer (a) next to said sample comprising a nitrile oxygen barrier resin formed by the polymerization of 55 to 90 weight percent of acrylonitrile with a remaining proportion of methylacrylate optionally in the presence of a preformed diene rubber, and a layer (b) comprising a material having a water vapor transmission rate equal to or less than 5.0.

19. The process as in claim 18 wherein the layer (a) has an oxygen transmission rate of less than 1.0.

* * * * *